(12) United States Patent
Khorram et al.

(10) Patent No.: US 12,122,848 B2
(45) Date of Patent: Oct. 22, 2024

(54) COMPOSITIONS AND METHODS FOR TREATING FIBROIDS

(71) Applicant: THE LUNDQUIST INSTITUTE FOR BIOMEDICAL INNOVATION AT HARBOR-UCLA MEDICAL CENTER, Torrance, CA (US)

(72) Inventors: Omid Khorram, Rolling Hills, CA (US); Tsai-Der Chuang, Inglewood, CA (US)

(73) Assignee: THE LUNDQUIST INSTITUTE FOR BIOMEDICAL INNOVATION AT HARBOR-UCLA MEDICAL CENTER, Torrance, CA (US)

( * ) Notice: Subject to any disclaimer, the term of this patent is extended or adjusted under 35 U.S.C. 154(b) by 355 days.

(21) Appl. No.: 17/365,723

(22) Filed: Jul. 1, 2021

(65) Prior Publication Data

US 2022/0010028 A1   Jan. 13, 2022

Related U.S. Application Data

(60) Provisional application No. 63/050,034, filed on Jul. 9, 2020.

(51) Int. Cl.
| | | |
|---|---|---|
| *C07K 16/40* | (2006.01) | |
| *A61K 31/4188* | (2006.01) | |
| *A61K 31/4245* | (2006.01) | |
| *A61K 31/4439* | (2006.01) | |
| *A61K 31/47* | (2006.01) | |
| *A61K 31/7105* | (2006.01) | |
| *A61P 15/00* | (2006.01) | |
| *A61P 19/04* | (2006.01) | |

(52) U.S. Cl.
CPC .......... *C07K 16/40* (2013.01); *A61K 31/4188* (2013.01); *A61K 31/4245* (2013.01); *A61K 31/4439* (2013.01); *A61K 31/47* (2013.01); *A61K 31/7105* (2013.01); *A61P 15/00* (2018.01); *A61P 19/04* (2018.01)

(58) Field of Classification Search
None
See application file for complete search history.

(56) References Cited

U.S. PATENT DOCUMENTS

| | | | |
|---|---|---|---|
| 2011/0159017 A1* | 6/2011 | Van Den Eynde | C12Q 1/6886 435/6.12 |
| 2020/0054673 A1* | 2/2020 | Ports | A61K 31/4245 |
| 2020/0283395 A1* | 9/2020 | Lefranc | C07D 239/28 |
| 2021/0030869 A1* | 2/2021 | Smith | A61K 39/3955 |

OTHER PUBLICATIONS

Medical Dictionaryweb.com (Leiomyoma 2012) (Year: 2012).*
Tsibris et al. (Fertility and Sterility Jul. 2002 78(1): 114-121) (Year: 2002).*
Dudek, K. (A Simple Guide to Fibroids, Nabata Health Apr. 18, 2019) (Year: 2019).*
Hutchinson et al. (Fertility and Sterility, Sep. 2020 114(3): SUPPL, pp. e339, No. P-567) (Year: 2020).*
Chuang et al. (Fertil Steril. Apr. 2024; 121(4):669-678) (Year: 2024).*
Chuang et al. (Fertil Steril. Jun. 9, 2021 ;116(4):1160-1169) (Year: 2021).*

* cited by examiner

*Primary Examiner* — Peter J Reddig
(74) *Attorney, Agent, or Firm* — Sheppard Mullin Richter & Hampton LLP

(57) ABSTRACT

The present disclosure relates generally to compositions and methods for treating fibroid in a patient in need thereof, which entails administering to the patient an effective amount of an agent that inhibits the expression or activity of TDO2 or IDO1.

7 Claims, 11 Drawing Sheets

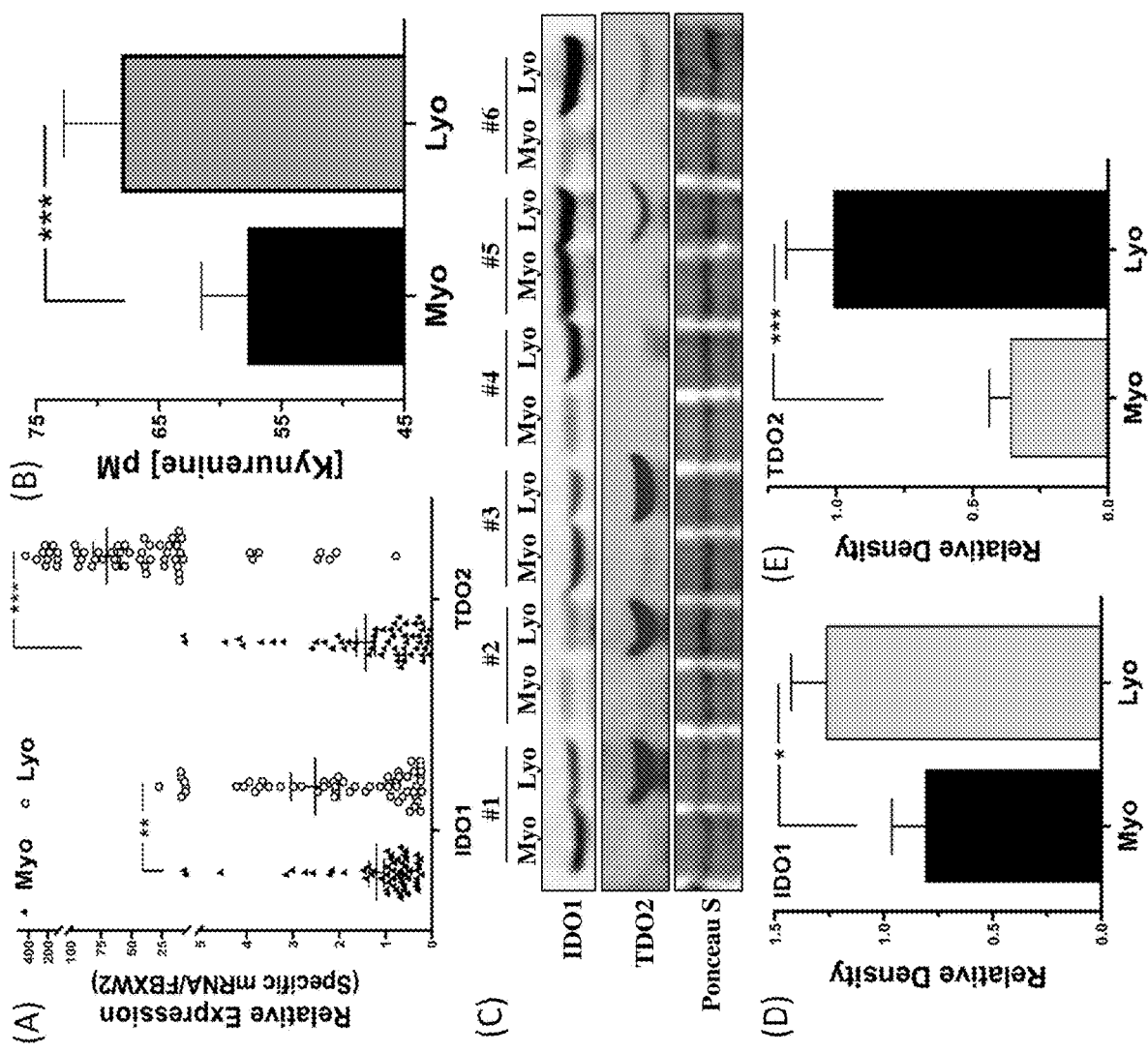
FIG. 1A-E

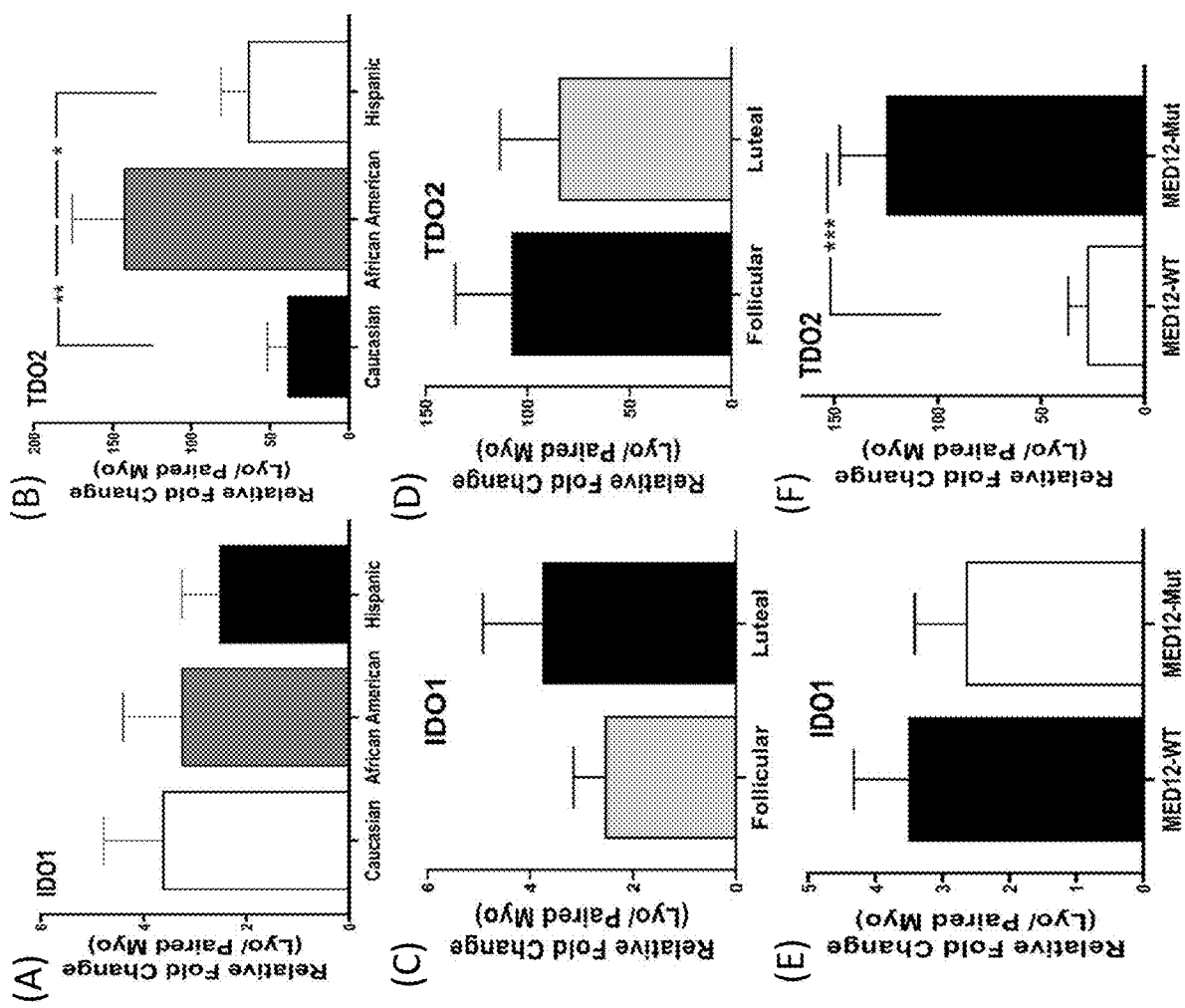
FIG. 2A-F

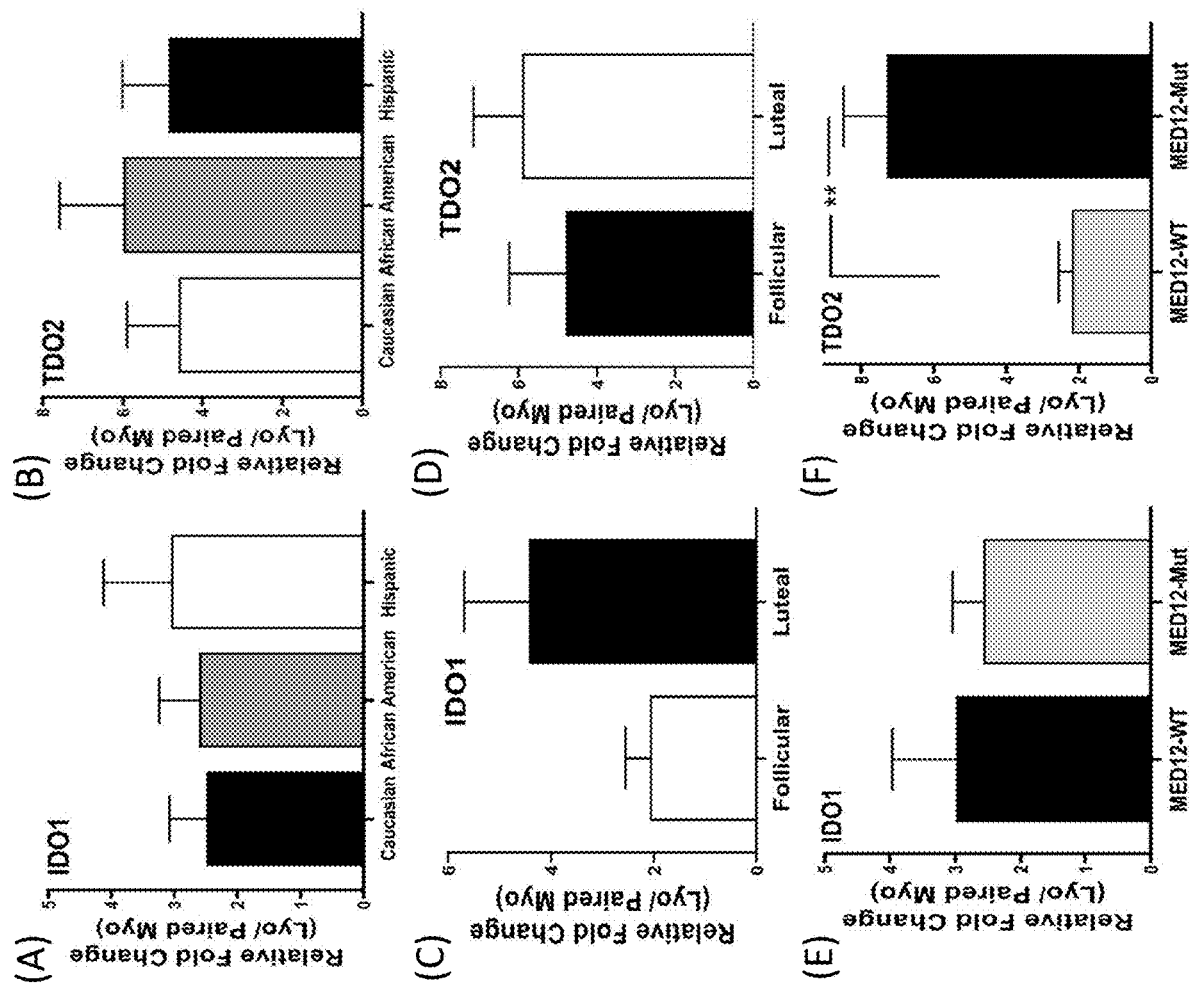
FIG. 3A-F

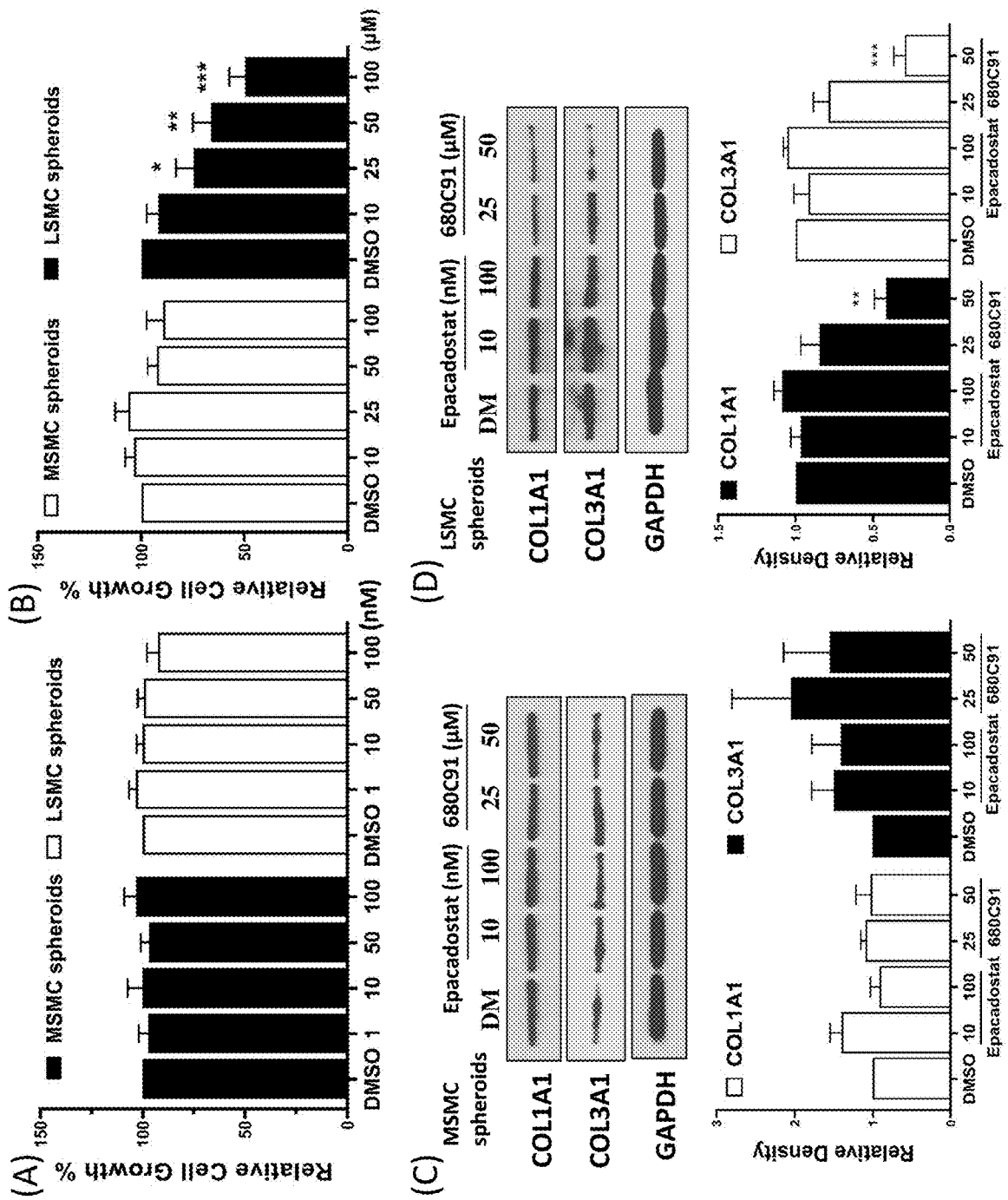
FIG. 4A-D

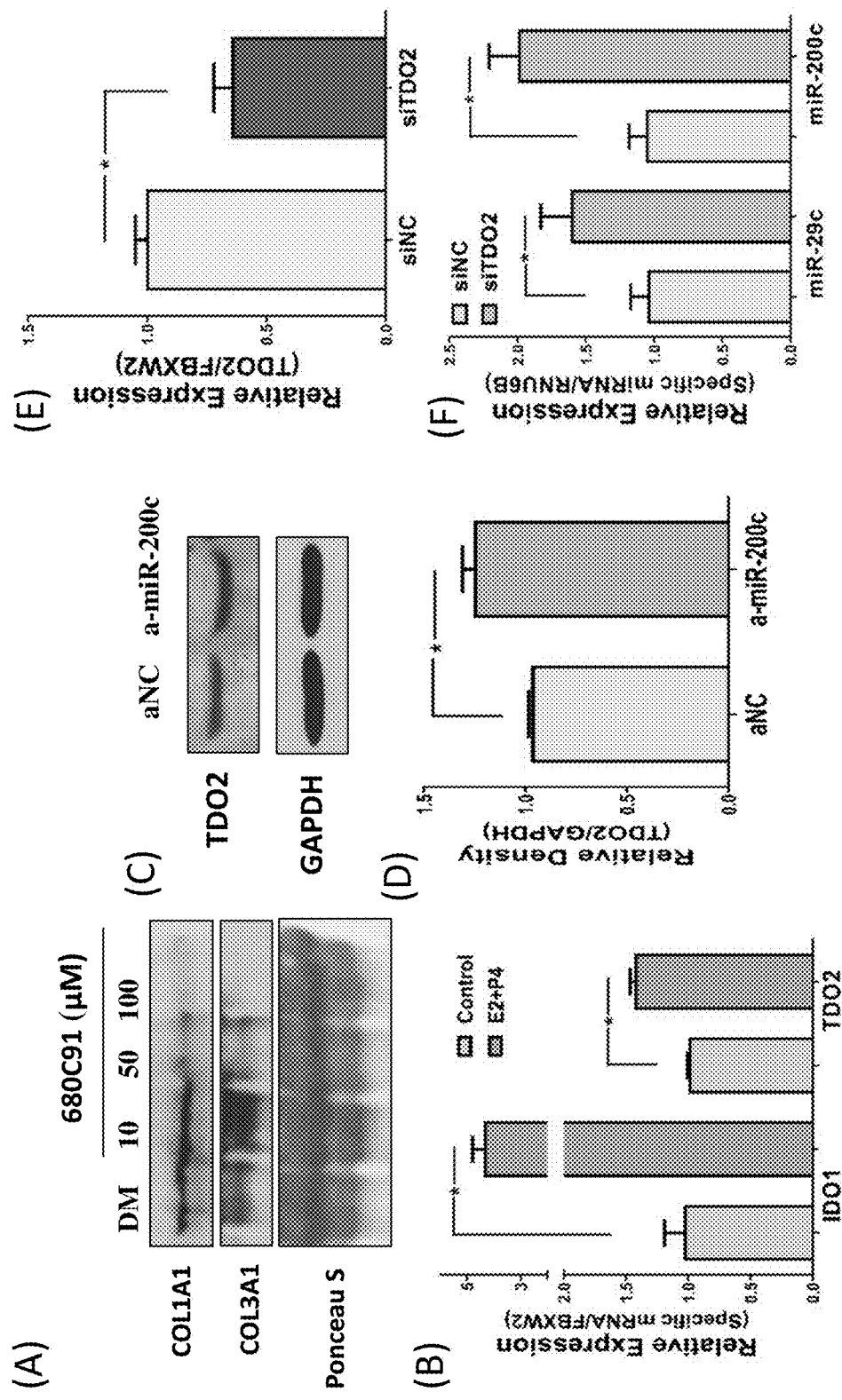
FIG. 5A-F

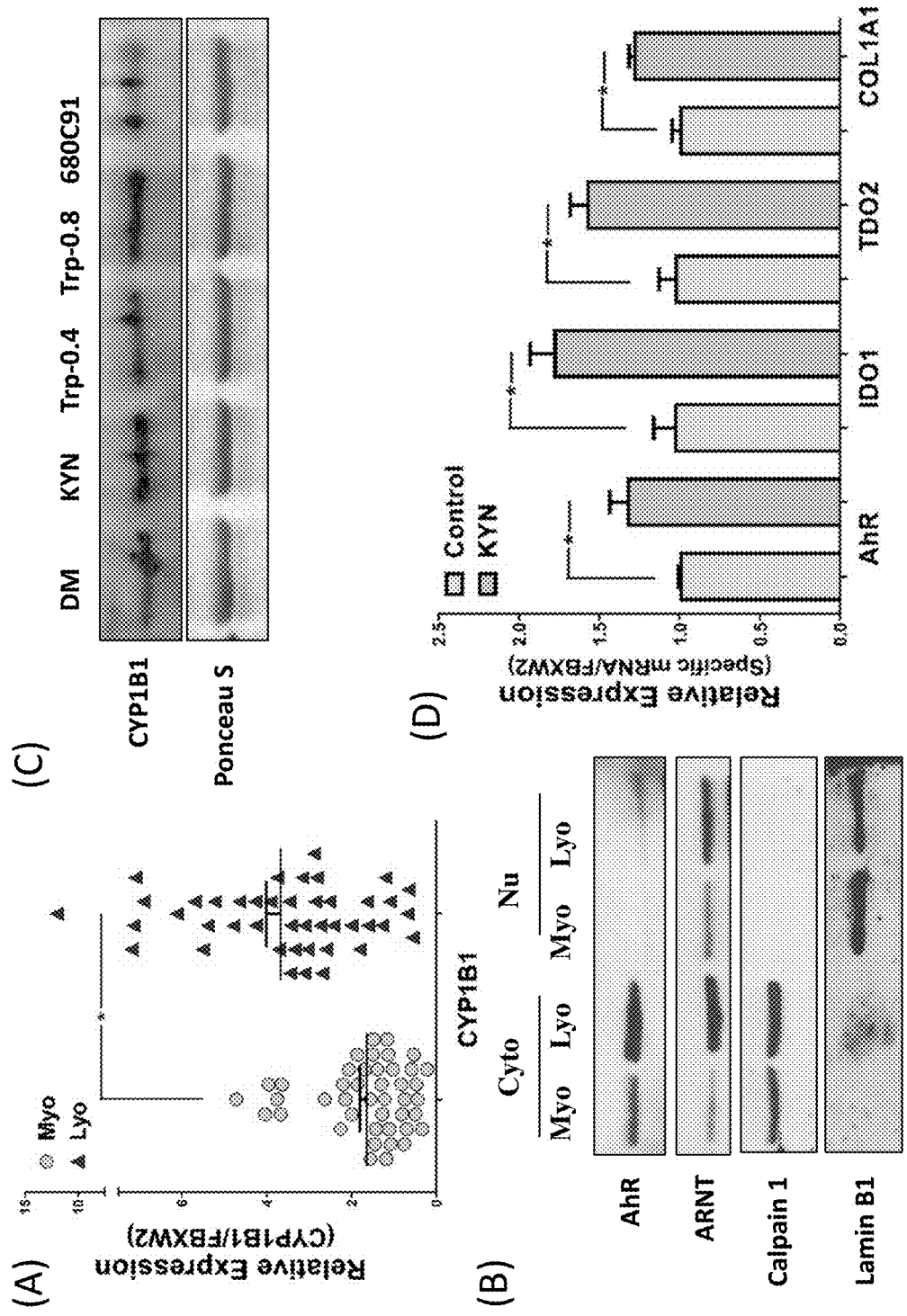
FIG. 6A-D

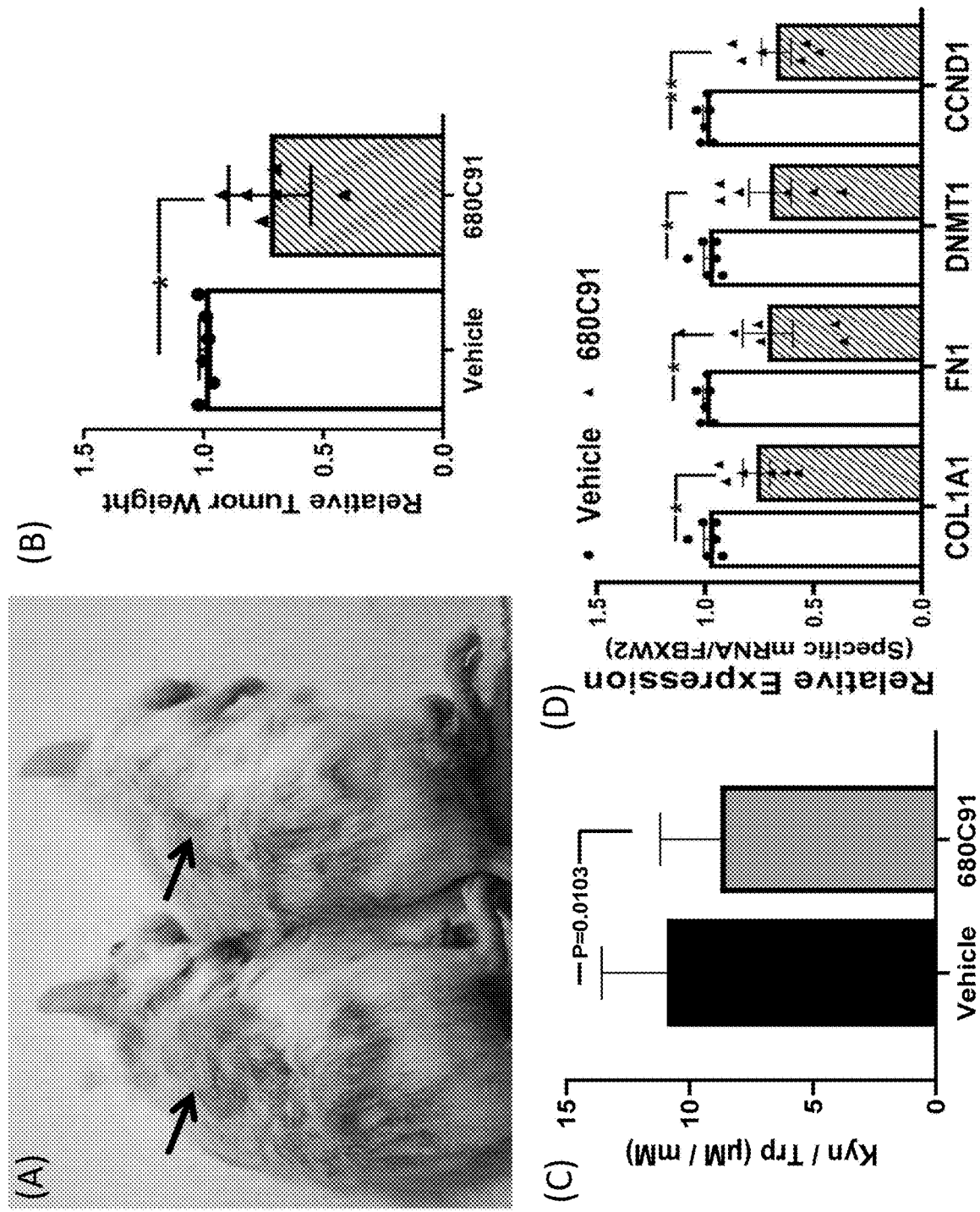
FIG. 7A-D

COMPOSITIONS AND METHODS FOR TREATING FIBROIDS

CROSS REFERENCE TO RELATED APPLICATIONS

This application claims the benefit under 35 U.S.C. § 119(e) of U.S. Provisional Application No. 63/050,034, filed Jul. 9, 2020, the content of which is incorporated by reference in its entirety into the present disclosure.

BACKGROUND

Fibroid is a benign tumor of muscular and fibrous tissues, typically developing in the wall of the uterus. Uterine fibroids, also known as uterine leiomyomas, are benign smooth muscle tumors of the uterus. Most women have no symptoms while others may have painful or heavy periods. If large enough, they may push on the bladder causing a frequent need to urinate. They may also cause pain during sex or lower back pain. A woman can have one uterine fibroid or many. Occasionally, fibroids may make it difficult to become pregnant, although this is uncommon.

The exact cause of uterine fibroids is unclear. However, fibroids run in families and appear to be partly determined by hormone levels. Risk factors include obesity and eating red meat. Diagnosis can be performed by pelvic examination or medical imaging.

About 20% to 80% of women develop fibroids by the age of 50. In 2013, it was estimated that 171 million women were affected worldwide. They are typically found during the middle and later reproductive years. After menopause, they usually decrease in size. In the United States, uterine fibroids are a common reason for surgical removal of the uterus.

Treatments typically focus on symptoms. NSAIDs, such as ibuprofen, may help with pain and bleeding. Iron supplements may be needed in those with heavy periods. Medications of the gonadotropin-releasing hormone agonist class may decrease the size of the fibroids but are expensive and associated with side effects. If greater symptoms are present, surgery to remove the fibroid or uterus may help. Uterine artery embolization may also help. Cancerous versions of fibroids are rare and are known as leiomyosarcomas.

Other attempted therapies include those that try to reduce estrogen/progesterone. However, such therapies are problematic because of the associated side effects and can only be used for short period of time. There is therefore a need for safe drugs that do not affect estrogen/progesterone and can be used for long term therapy.

SUMMARY

The present disclosure, in one embodiment, a method of treating fibroid in a patient in need thereof, comprising administering to the patient an effective amount of an agent that inhibits the expression or activity of TDO2 (tryptophan 2,3-dioxygenase) or IDO1 (indoleamine-pyrrole 2,3-dioxygenase).

In some embodiments, the agent is a gene editing complex comprising a polynucleotide for inactivating the gene of TDO2 o IDO1. In some embodiments, the agent is a siRNA, miRNA, or antisense RNA that inhibits the expression of TDO2 or IDO1. In some embodiments, the agent is an anti-TDO2 or anti-IDO1 antibody.

In some embodiments, the agent is a TDO2 inhibitor, such as 680C91. In some embodiments, the agent is an IDO1 inhibitor, such as Epacadostat (INCB24360), navoximod (GDC-0919) and BMS-986205. In some embodiments, the agent does not reduce estrogen or progesterone in the patient. In some embodiments, the patient has a mutation in the mediator complex subunit 12 gene (MED12). Examples include c.130G>C (p.Gly44Arg), c.130G>A (p.Gly44Ser), c.130G>T (p.Gly44Cys), c.131G>C (p.Gly44Ala), c.131G>A (p.Gly44Asp), and c.131G>T (p.Gly44Val).

In some embodiments, the fibroid is a uterine fibroid. In some embodiments, the uterine fibroid is selected from the group consisting of intramural fibroid, subserosal fibroid, subserosal tumor, or submucosal fibroid.

In some embodiments, the method ameliorates at least a symptom selected from the group consisting of heavy bleeding between or during periods that includes blood clots, pain in the pelvis or lower back, increased menstrual cramping, increased urination, pain during intercourse, menstruation that lasts longer than usual, pressure or fullness in your lower abdomen, and swelling or enlargement of the abdomen.

In some embodiments, the patient is Caucasian and the agent inhibits the expression or activity of IDO1. In some embodiments, the patient is African American or Hispanic and the agent inhibits the expression or activity of TDO2.

Without limitation, the administration can be oral, intravenous, intramuscular, subcutaneous, or local injection to the fibroid.

BRIEF DESCRIPTION OF THE DRAWINGS

FIG. 1A-F. (A) The expression of IDO1 and TDO2 in 58 paired myometrium (Myo) and leiomyoma (Lyo). The results in this and subsequent figures are presented as mean±SEM with P values (*$P<0.05$; $P<0.01$ and *$P<0.001$) indicated by corresponding lines. (B) Kynurenine levels as determined by ELISA in 46 paired myometrium (Myo) and leiomyoma (Lyo). (C) Western blot analysis of IDO1 and TDO2 in paired (n=50) myometrium (Myo) and leiomyoma (Lyo) with bar graphs for IDO1 (D) and TDO2 (E) showing their relative band densities in myometrium and leiomyoma. (F) Localization of IDO1 (×400) and TDO2 (×400) in myometrium and leiomyoma as determined by immunohistochemistry.

FIG. 2A-F. Relative mRNA expression of IDO1 (A; C; E) and TDO2 (B; D; F) expressed as fold change (Lyo/paired Myo) based on race/ethnicity in Caucasian (n=12), African American (n=25) and Hispanics (n=21) (A-B); menstrual cycle phase in proliferative phase (n=27) and secretory phase (n=14) (C-D); MED12 mutation status in wild type (n=19) and MED12 bearing mutations (n=39) (E-F). The results are presented as mean±SEM with P values (*$P<0.05$; $P<0.01$ and *$P<0.001$) indicated by corresponding lines.

FIG. 3A-F. Relative protein expression of IDO1 (A; C; E) and TDO2 (B; D; F) expressed as fold change (Lyo/paired Myo) based on race/ethnicity in Caucasian (n=12), African American (n=20) and Hispanics (n=18) (A-B); menstrual cycle phase in proliferative phase (n=19) and secretory phase (n=15) (C-D); MED12 mutation status in wild type (n=20) and MED12 bearing mutations (n=30) (E-F). The results are presented as mean±SEM with P values (**$P<0.01$) indicated by corresponding lines.

FIG. 4A-E. The effect of IDO1 inhibitor Epacadostat (A) and TDO2 inhibitor 680C91 (B) on MSMC and LSMC spheroids cell proliferation as determined by the CellTiter-Glo 3D Cell Viability Assay (n=4). (C-D) Representative immunoblots demonstrating COL1A1 and COL3A1 expression following 48 hours treatment with different concentrations of IDO1 inhibitor (Epacadostat) and TDO2 inhibitor (680C91) in MSMC spheroids (C) and LSMC spheroids (D) with bar graphs show the relative protein band densities (n=4). (E) Representative of immunoblotting of fibronectin (FN1), IKBKB and NF-kB (p65) expression in LSMC spheroids treated with different doses of TDO2 inhibitor 680C91 for 48 h (N=3). The results are presented as mean±SEM of independent experiments. *P<0.05; P<0.01; *P<0.001.

FIG. 5A-F. (A) Representative images of COL1A1 and COL3A1 in culture-conditioned media of leiomyoma explants after treatment with different doses of TDO2 inhibitor, 680C91 for 48 hours (N=2). An equal volume of conditioned media was used, and a Ponceau S-stained protein band on the nitrocellulose membrane was used as a loading control. (B) The effect of DMSO (control) and E2+P4 ($10^{-8}$M each) after 48 hours of culture on the expression of IDO1 and TDO2 in LSMC spheroids (N=2). (C) Representative western blot analysis of TDO2 following transfection of LSMC spheroids with anti-miR-200c oligonucleotides for 96 hrs. Bar graph (D) shows the relative band densities of TDO2. (E-F) QRT-PCR analysis of TDO2 (E), miR-29c and miR-200c (F) in LSMC spheroids after transfection of siRNA negative control (siNC) or TDO2 siRNA oligonucleotides (siTDO2) for 96 hours (N=3). The results are presented as mean±SEM with P values (*:p<0.05) indicated by corresponding lines.

FIG. 6A-D. (A) The relative (mean±SEM) expression of CYP1B1 in paired (N=43) myometrium (Myo) and leiomyoma (Lyo). (B) Representative images show the levels of AhR and ARNT in fresh subfractionated cytoplasmic (Cyto) and nuclear (Nu) phase from myometrium (Myo) and paired leiomyoma (Lyo) with Calpain 1 and Lamin B1 served as markers for the respective subcellular fractions (N=3). (C) Representative images of CYP1B1 in leiomyoma explants after treatment with kynurenine (100 μM), different doses of tryptophan (mM) and TDO2 inhibitor (680C91, 50 μM) for 48 hours with a Ponceau S-stained protein band on the nitrocellulose membrane used as a loading control (N=2). (D) The effect of kynurenine (KYN, 100 μM) treatment for 72 hours on the expression of AhR, IDO1, TDO2 and COL1A1 in LSMC spheroids (N=2). The results are presented as mean±SEM with P values (*:p<0.05) indicated by corresponding lines.

FIG. 7A-E. (A) Representative of the gross appearance of leiomyoma specimens (arrow) implanted subcutaneously in CB-17 SCID/Beige female mice following 8 weeks treatment of vehicle (left) or TDO2 inhibitor (right; 680C91; 10 mg/Kg daily via IP). (B) The relative explants weight between vehicle and 680C91 treated group after 8 weeks treatment (n=6). The ratio of plasma kynurenine vs tryptophan levels was shown in (C). (D) QRT-PCR analysis of COL1A1, FN1, DNMT1 and CCND1 expression in explants (n=6) implanted subcutaneously after 8 weeks treatment of vehicle or TDO2 inhibitor. (E) Paraformaldehyde-fixed paraffin-embedded xenograft explants of vehicle (a) or TDO2 inhibitor (b) stained with Masson's Trichrome reagent. The representative images show less deposition of collagens (blue), keratin (red) and cytoplasm (red) in TDO2 inhibitor treated explants (n=6). The results are presented as mean±SEM with P values (*:p<0.05) indicated by corresponding lines.

Figure 1F:
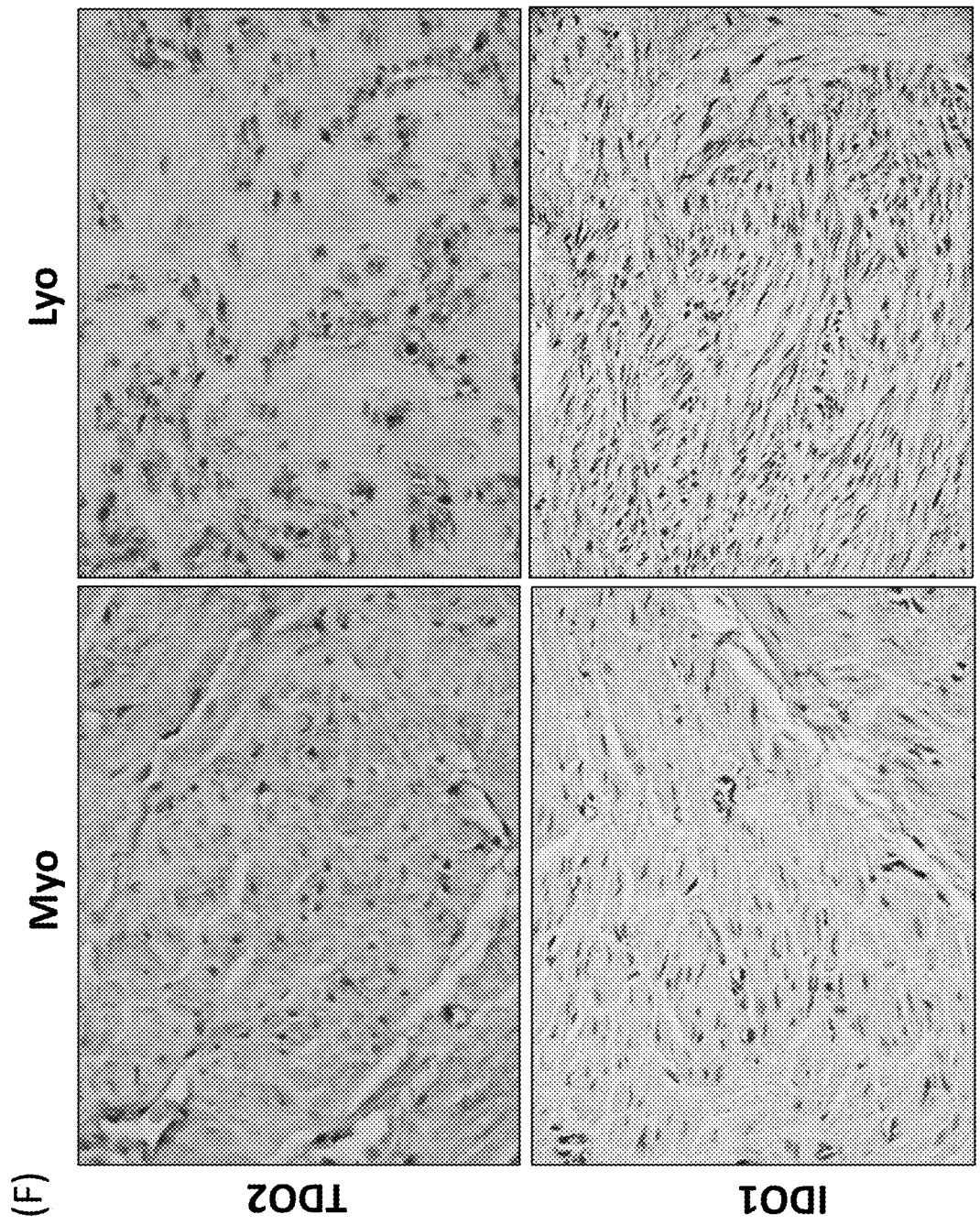

It will be recognized that some or all of the figures are schematic representations for purpose of illustration.

DETAILED DESCRIPTION

Definitions

The following description sets forth exemplary embodiments of the present technology. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition of fibroids. The therapeutically effective amount may vary depending on the subject, and disease or condition being treated, the weight and age of the subject, the severity of the disease or condition, and the manner of administering, which can readily be determined by one or ordinary skill in the art.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Treatment of Fibroids by Inhibiting TDO2 or IDO1

It is herein discovered that inhibitors of the TDO2 enzyme can be effective in shrinking the size of fibroid tumors and potentially associated symptoms of these tumors such as excessive uterine bleeding, pain, pelvic pressure and infertility. As demonstrated in the experimental examples, the expression of TDO2 was increased by over 150 fold in fibroid tumors. The TDO2 inhibitor 680C91 inhibited the expression of TDO2 in fibroids resulting in decreased expression of Collagen type I and III, TGF-β3, and inhibited fibroid cell proliferation, leading to tumor shrinkage. Likewise, the expression of IDO1 was also increased in such tumors, the inhibition of which resulted in suppression of proliferation of leiomyoma smooth muscle cell spheroids, as compared to control (myometrial smooth muscle cells).

Also interestingly, the overexpression of TDO2 was more pronounced in predict African Americans and Hispanics while IDO1 overexpression was more pronounced in Caucasians. It is contemplated that TDO2 inhibitors would be more effective among African American and Hispanic fibroid patients while IDO1 inhibitors would be more effective among Caucasian.

In some embodiments, the agent does not reduce estrogen or progesterone in the patient. In some embodiments, the patient has a mutation in the mediator complex subunit 12 gene (MED12). Examples include c.130G>C (p.Gly44Arg), c.130G>A (p Gly44 Ser), c. 130G>T (p Gly44Cys), c.131G>C (p Gly44A1a), c.131G>A (p.Gly44Asp), and c.131G>T (p.Gly44Val).

Figure 8:
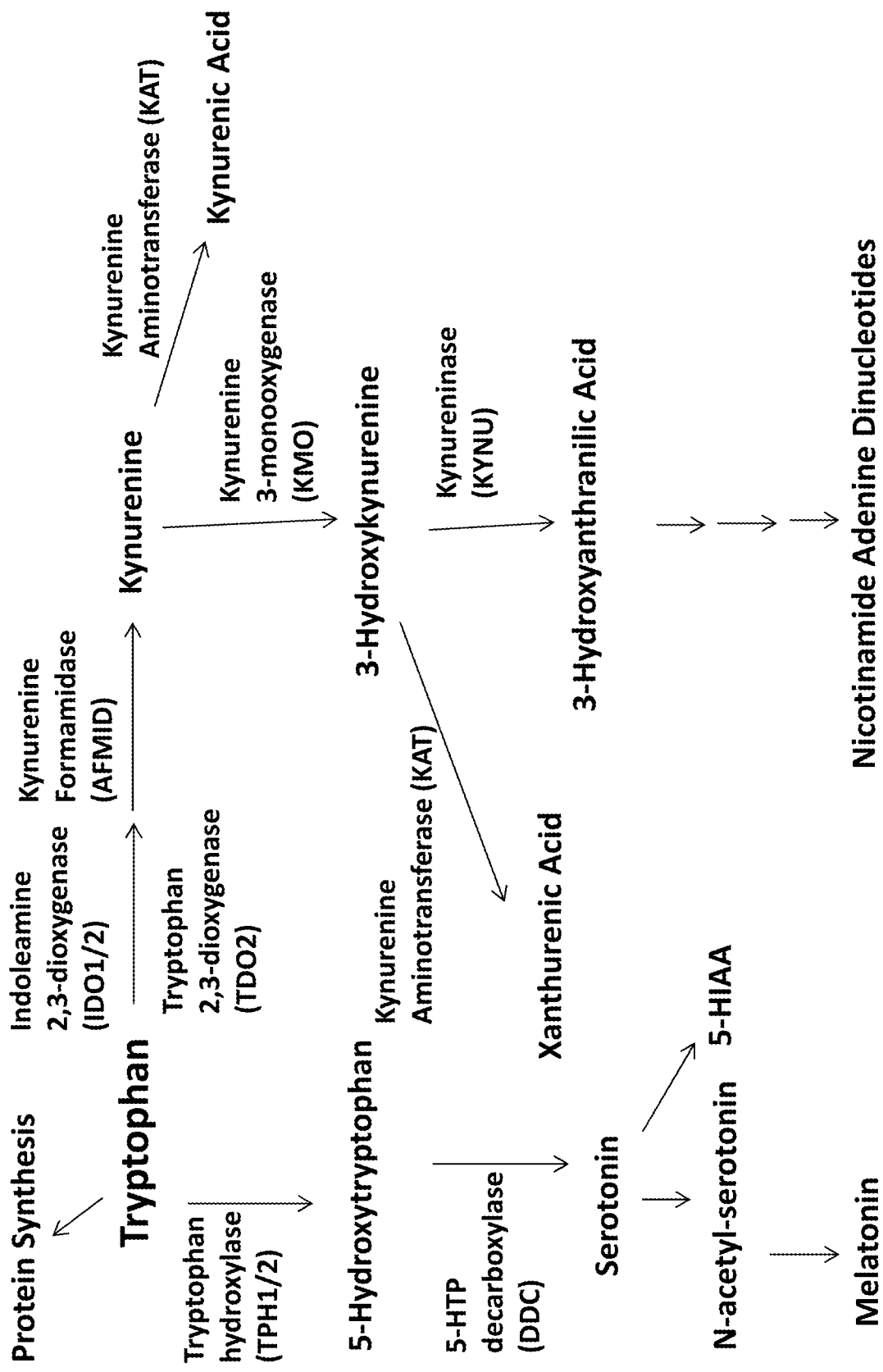
FIG. 8 illustrates the biological pathways relating to tryptophan degradation.

In accordance with one embodiment of the present disclosure, provided is a method of treating fibroid in a patient in need thereof, which entails administering to the patient an effective amount of an agent that inhibits tryptophan degradation along the kynurenine pathway (illustrated in FIG. 8). In some embodiments, the agent inhibits the expression or activity of TDO2 (tryptophan 2,3-dioxygenase) or IDO1 (indoleamine-pyrrole 2,3-dioxygenase).

As provided, fibroid is a benign tumor of muscular and fibrous tissues, typically developing in the wall of the uterus. Uterine fibroids are benign smooth muscle tumors of the uterus. The type of fibroid a woman develops depends on its location in or on the uterus.

Intramural fibroids are the most common type of fibroid. These types appear within the muscular wall of the uterus. Intramural fibroids may grow larger and can stretch patient's uterus.

Subserosal fibroids form on the outside of the uterus, which is called the serosa. They may grow large enough to make patient's uterus appear bigger on one side.

Subserosal tumors can develop a stem, a slender base that supports the tumor. When they do, they're known as pedunculated fibroids.

Submucosal fibroids develop in the middle muscle layer, or myometrium, of your uterus. Submucosal tumors aren't as common as the other types. These tumors distort the uterine cavity; even small lesions in this location may lead to bleeding and infertility. A pedunculated lesion within the cavity is termed an intracavitary fibroid and can be passed through the cervix.

In one embodiment, the compositions and methods of the present disclosure are useful for treating intramural fibroids, subserosal fibroids, and submucosal fibroids. In one embodiment, the compositions and methods of the present disclosure are useful for treating one or more symptoms of fibroid. Examples of such symptoms include, without limitation, heavy bleeding between or during periods that includes blood clots, pain in the pelvis or lower back, increased menstrual cramping, increased urination, pain during intercourse, menstruation that lasts longer than usual, pressure or fullness in your lower abdomen, and swelling or enlargement of the abdomen.

Tryptophan 2,3-dioxygenase, or TDO (or TDO2), (EC 1.13.11.11) is a heme enzyme that catalyzes the oxidation of L-tryptophan (L-Trp) to N-formyl-L-kynurenine, as the first and rate-limiting step of the kynurenine pathway. TDO plays a central role in the physiological regulation of tryptophan flux in the human body, as part of the overall biological process of tryptophan metabolism. TDO catalyzes the first and rate-limiting step of tryptophan degradation along the kynurenine pathway and thereby regulates systemic tryptophan levels. In humans, tryptophan 2,3-dioxygenase is encoded by the TDO2 gene. The related biochemical reactions and molecules are illustrated in FIG. 8. A representative protein sequence of TDO2 is NP 005642 and a representative mRNA sequence is NM 005651.

Indoleamine-pyrrole 2,3-dioxygenase (IDO, IDO1, or INDO EC 1.13.11.52) is a heme-containing enzyme physiologically expressed in a number of tissues and cells, such as the small intestine, lungs, female genital tract or placenta. In humans IDO is encoded by the IDO1 gene. IDO is involved in tryptophan metabolism. It is one of three enzymes that catalyze the first and rate-limiting step in the kynurenine pathway, the 02-dependent oxidation of L-tryptophan to N-formylkynurenine, the others being indolamine-2,3-dioxygenase (IDO2) and tryptophan 2,3-dioxygenase (TDO). A representative protein sequence of IDO1 is NP 002155 and a representative mRNA sequence is NM_002164.

Agents that inhibit the expression or activity of TDO2 or IDO1 are known in the art.

On example is a gene editing system which can introduce a mutation to the active site, a premature stop codon or a frameshift mutation into the TDO2 or IDO1 gene. Gene editing technologies may include, but are not limited to, a CRISPR/Cas9 system, a CRISPR/Cas13 system, a zinc finger nuclease system, a TALEN system, and a meganuclease system. These gene editing technologies themselves are described in public domain (e.g., U.S. Pat. No. 10,196,652, Science: Vol. 358, Issue 6366, pp. 1019-1027).

In some embodiments, the TDO2 or IDO1 inhibitor is one or more components of a gene editing system targeting one or more sites within a gene encoding TDO2 or IDO1 or a regulatory element thereof, a nucleic acid molecule encoding the one or more components of the gene editing system, or a combination thereof. In some embodiments, the gene editing system is a CRISPR/Cas9 system. In some embodiments, the gene editing system is a CRISPR/Cas13 system. In some embodiments, the gene editing system is a zinc finger nuclease system. In some embodiments, the gene editing system is a TALEN system. In some embodiments, the gene editing system is a meganuclease system. In some embodiments, the TDO2 or IDO1 inhibitor comprises a guide RNA molecule comprising a tracer and a crRNA. In some embodiments, the crRNA comprises a targeting domain that is complementary with a target sequence of TDO2 or IDO1.

Another example of agents that inhibit the expression or activity of a gene is through the RNA interference (RNAi) process in which RNA molecules inhibit gene expression or translation, by neutralizing targeted mRNA molecules. Two types of small ribonucleic acid (RNA) molecules—microRNA (miRNA) and small interfering RNA (siRNA)—are typical to RNA interference.

The RNAi process is initiated by the enzyme Dicer, which cleaves long double-stranded RNA (dsRNA) molecules into short double-stranded fragments of ~21 nucleotide siRNAs. Each siRNA is unwound into two single-stranded RNAs (ssRNAs), the passenger strand and the guide strand. The passenger strand is degraded and the guide strand is incorporated into the RNA-induced silencing complex (RISC).

Another example is a microRNA (miRNA) which is a small non-coding RNA molecule (containing about 22 nucleotides) found in plants, animals and some viruses, that functions in RNA silencing and post-transcriptional regulation of gene expression. miRNAs function via base-pairing with complementary sequences within mRNA molecules. As a result, these mRNA molecules are silenced, by one or more of the following processes: (1) Cleavage of the mRNA strand into two pieces, (2) Destabilization of the mRNA through shortening of its poly(A) tail, and (3) Less efficient translation of the mRNA into proteins by ribosomes.

Still other examples include ribozymes and antisense RNA, which can be designed with knowledge well known in the art for inhibiting the expression of a target protein.

In another embodiment, the agent is an antibody or antigen-binding fragment thereof against TDO2 or IDO1. As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as F(ab')$_2$, F(ab)$_2$, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex.

Small molecule inhibitors of TDO2 and IDO1 are also known in the art. 680C91 is of the compounds in a series of TDO2 inhibitors initially developed by Madge and Salter for depression therapy, characterized by a (fluoro)indole scaffold substituted in the 3-position by a pyridinyl-vinyl side chain (Schmidt S K, et al. (2009) *Eur J Immunol* 39:2755-2764). 680C91 has a chemical name of 6-Fluoro-3-[(1E)-2-(3-pyridinyl)ethenyl]-1H-indole and a structure of:

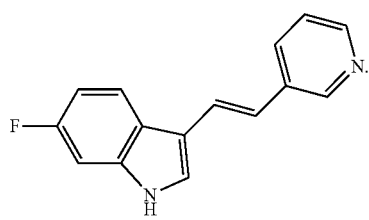 [SMILES: Fc1ccc2c(/C=C/c3cccnc3)c[nH]c2c1]

Additional, potent TDO2 inhibitors are described in Pei et al., ACS Med. Chem. Lett. 2018, 9, 417-421, some of which are shown below.

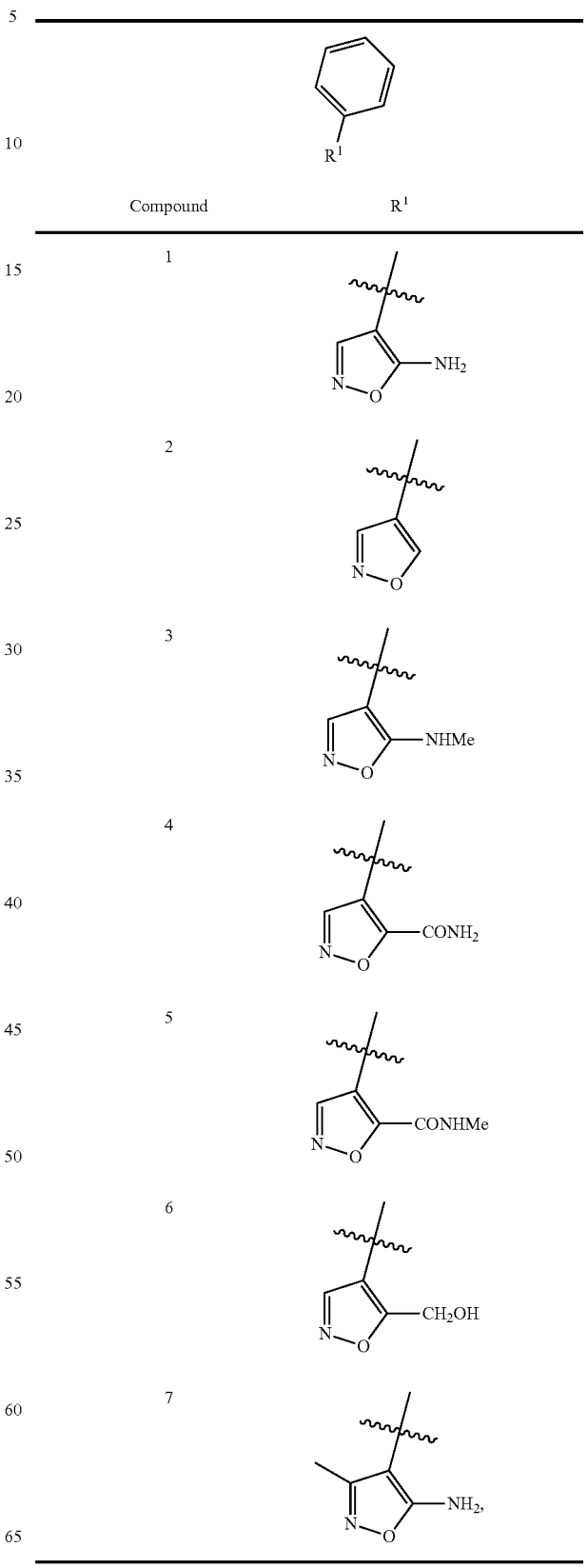

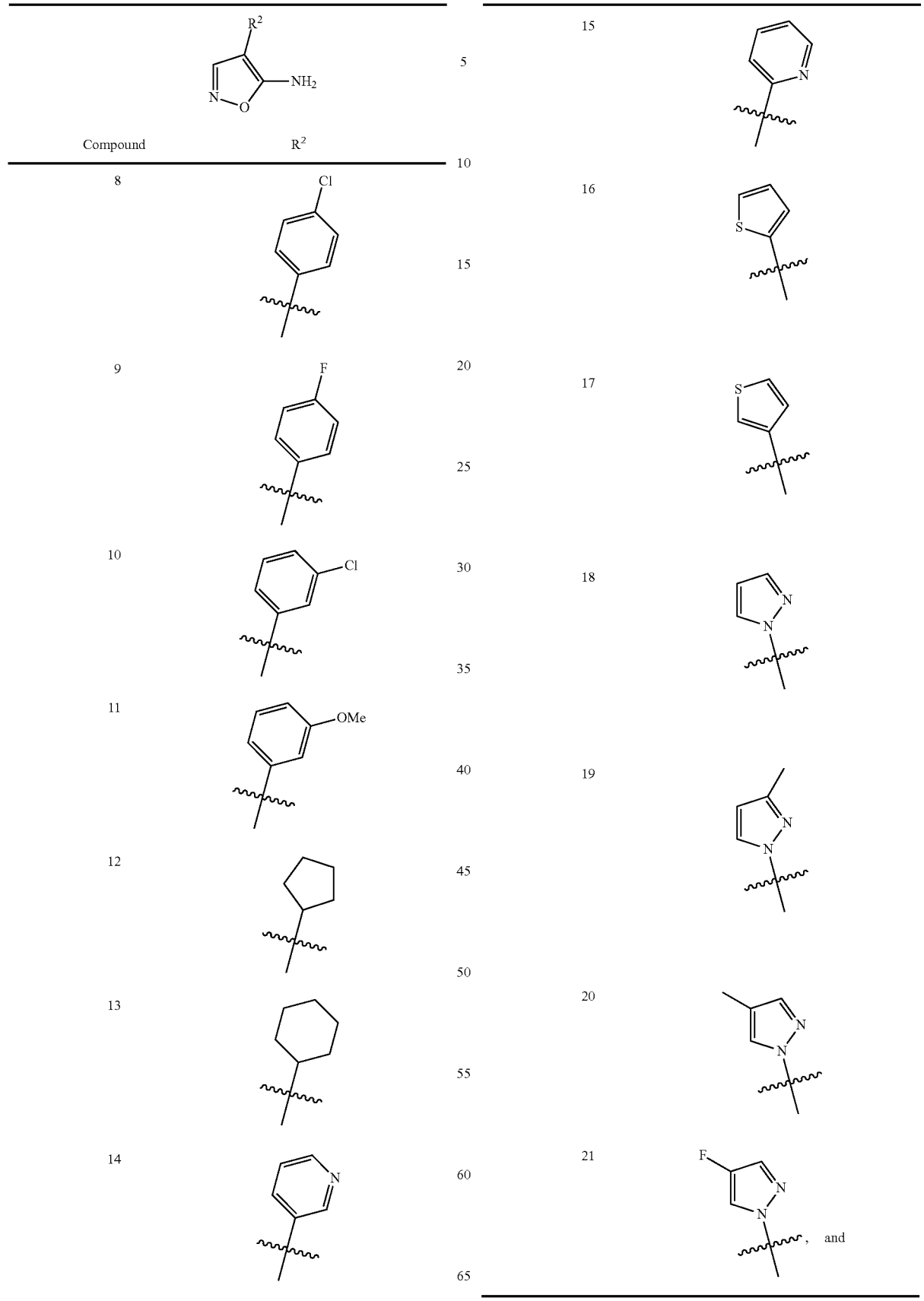

-continued

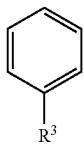

| Compound | R³ |
|---|---|
| 21 | 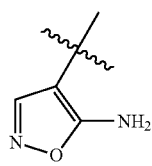 |
| 22 | 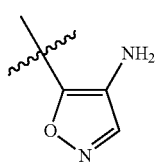 [SMILES: *c1oncc1N] |
| 23 | 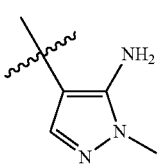 [SMILES: *c1cnn(C)c1N] |
| 24 | 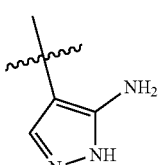 |
| 25 | 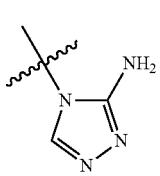 [SMILES: *n1cnnc1N] |
| 26 | 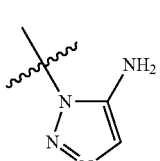 |
| 27 | 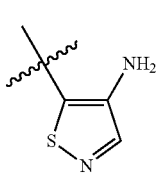 [SMILES: *c1sncc1N] |
| 28 | 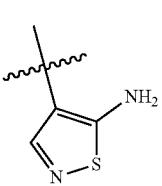 [SMILES: *c1cnsc1N] |
| 29 | 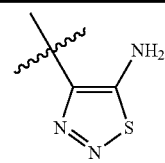 |
| 30 | 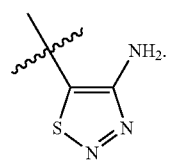 [SMILES: *c1snnc1N] |

Additional TDO2 inhibitors are disclosed in patent applications WO 2016026772 A1, WO 2015082499 A2, WO 2016071293 A2, WO 2016131381, WO 2017007700 A1, US20190016726A1 and US20200123163A1.

Epacadostat (INCB24360) and navoximod (GDC-0919) are potent IDO1 inhibitors and are in clinical trials for various cancers. BMS-986205 is also in clinical trials for cancer.

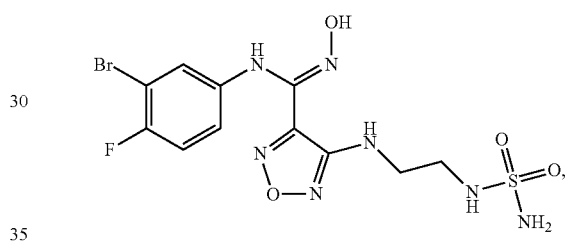
(Epacadostat)

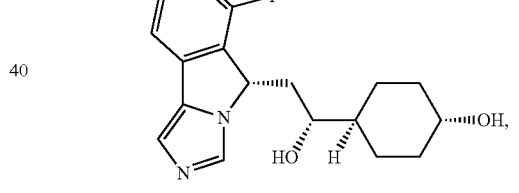
(navoximod)

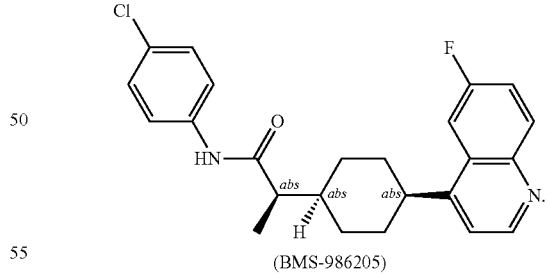
(BMS-986205)

Dual TDO2/IDO1 inhibitors are also under development. Examples are provided in, e.g., Sari et al., Molecules 2019, 24, 4346; doi:10.3390/molecules24234346.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

Pharmaceutical Compositions and Modes of Administration

Compounds provided herein are usually administered in the form of pharmaceutical compositions. Thus, provided herein are also pharmaceutical compositions that contain one or more of the compounds described herein or a pharmaceutically acceptable salt, tautomer, stereoisomer, mixture of stereoisomers, prodrug, or deuterated analog thereof and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein or a pharmaceutically acceptable salt, tautomer, stereoisomer, mixture of stereoisomers, prodrug, or deuterated analog thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound described herein or a pharmaceutically acceptable salt, tautomer, stereoisomer, mixture of stereoisomers, prodrug, or deuterated analog thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or a pharmaceutically acceptable salt, tautomer, stereoisomer, mixture of stereoisomers, prodrug, or deuterated analog thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Dosing

The specific dose level of a compound of the present application for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein administered per dose or per day. Daily dosage of a compound of Formula I may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

When administered orally, the total daily dosage for a human subject may be between 1 mg and 1,000 mg, between about 1,000-2,000 mg/day, between about 10-500 mg/day, between about 50-300 mg/day, between about 75-200 mg/day, or between about 100-150 mg/day.

The compounds of the present application or the compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are well known in cancer chemotherapy, and are frequently alternated with resting periods of about 1 to 28 days, commonly about 7 days or about 14 days, between cycles. The treatment cycles, in other embodiments, may also be continuous.

In a particular embodiment, the method comprises administering to the subject an initial daily dose of about 1 to 800 mg of a compound described herein and increasing the dose by increments until clinical efficacy is achieved. Increments of about 5, 10, 25, 50, or 100 mg can be used to increase the dose. The dosage can be increased daily, every other day, twice per week, or once per week.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

Example 1: Expression of TDO2 and IDO1

This example tested the expression of TDO2 and IDO2 in leiomyoma and matched myometrium.

Using paired leiomyoma and matched myometrium (N=43), the expression of TDO2 and IDO1 mRNA in the same specimens was determined. The analysis indicated that leiomyoma expressed elevated TDO2 and IDO1. Based on race/ethnicity the analysis by fold change (leiomyoma vs. matched myometrium) indicated a statistically significant difference between African American group (N=16) and Caucasian group (N=14) and a trend for higher increment in Hispanics (N=13) as compared with Caucasians in TDO2 expression, while no significant racial/ethnic differences in expression of IDO1 were found. Similarly, the representative protein levels (mixed races) of TDO2 and IDO1 determined by Western blot in a more limited number of samples and immunohistochemistry showed an increase in expression of TDO2 and IDO1 in leiomyoma as compared with paired myometrium. Both enzymes were expressed in smooth muscle cells of myometrium and blood vessels, fibroblasts and lymphocytes.

The ELISA analysis of nicotinamide adenine dinucleotide (NAD) and kynurenine concentration in paired (N=6) myometrium (Myo) and leiomyoma (Lyo) from untreated group was conducted. The result shows the effect of kynurenine (KYN, 100 µM) treatment for 72 hours on the expression of AhR, IDO1, TDO2 and COL1A1 in LSMC spheroids (N=2).

The effect of DMSO (control) and E2+P4 (estrogen/progesterone, $10^{-8}$M each) after 48 hours of culture on the expression of IDO1 and TDO2 in LSMC spheroids (N=2) was tested. QRT-PCR analysis of TDO2, miR-29c and miR-200c in LSMC spheroids after transfection of siRNA negative control (siNC) or TDO2 siRNA oligonucleotides (siTDO2) for 96 hours (N=3) confirms the effect of the siRNA. The results were also confirmed by Western.

Example 2: Effects of TDO2 and IDO1 Inhibition

This example tested the effect of inhibiting TDO2 and IDO2 on cell proliferation in MSMC (myometrial smooth muscle cells) and LSMC (leiomyoma smooth muscle cells) spheroids.

The effect of IDO1 inhibitor (epacadostat) and TDO2 inhibitor (680C91) on cell proliferation in MSMC and LSMC spheroids was determined. Both inhibitors significantly suppressed MSMC and LSMC cell proliferation, with a more pronounced effect in LSMC spheroids. Moreover, protein expression of genes associated with extracellular matrix (COL3A1 and fibronectin) and inflammation (IKBKB and NF-kB p65) were down-regulated dose dependently following treatment of LSMC spheroids with the TDO2 inhibitor 680C91.

This example also performed a preliminary experiment using freshly collected leiomyoma explants implanted subcutaneously on the flank of ovariectomized CB-17 scid/beige female mice (N=2), and treated with vehicle or TDO2 inhibitor (680C91; 8 mg/Kg daily via IP) for 8 weeks. After sacrifice, plasma was collected and analyzed for blood chemistry panel (Abaxis). The results show that 680C91 reduced tumor size. The results also showed there were no adverse effects on blood chemistry including liver and renal panels. Furthermore, there were no effects on body weight or food consumption of the animals treated with the inhibitor indicating drug safety albeit based on a limited number of mice. Following treatment with the TDO2 inhibitor, TDO2 expression was down-regulated, an expression of genes related to extracellular matrix (COL1A1 and TGF-β3) and inflammation (MyD88) were down-regulated supporting its usefulness for fibroid therapy.

Example 3: Tryptophan Catabolism is Dysregulated in Leiomyomas

This example expands on the experiments performed in Examples 1 and 2. In this example, leiomyoma, as compared with matched myometrium, expressed significantly higher levels of IDO1 and TDO2 mRNA (60.3%, 35/58 pairs; 98.3%, 57/58 pairs, respectively) and protein (54%, 27/50 pairs; 92%, 46/50 pairs, respectively), and kyneurenine (KYN; 78.3%, 36/46 pairs), a marker of enzyme activity. The expression of TDO2 but not IDO1 mRNA was significantly higher in fibroids from African American (AA) as compared with Caucasian and Hispanic patients. TDO2 but not IDO1 protein and mRNA levels were more abundant in fibroids bearing the MED12 mutation as compared with wild type leiomyomas. Treatment of LSMC (leiomyoma smooth muscle cells) and MSMC (myometrial smooth muscle cells) spheroids with the TDO2 inhibitor, 680C91 but not the IDO1 inhibitor, epacadostat significantly repressed cell proliferation and the expression of collagen type I (COL1A1) and type III (COL3A1) in a dose-dependent manner; these effects were more pronounced in LSMC as compared with MSMC spheroids.

Leiomyomas are benign uterine tumors with fibrotic characteristic. Although their etiology remains unknown, leiomyoma develop in ~70% women during reproductive years with a higher prevalence and symptom severity in African Americans (AA). Risk factors for fibroids are race, age, premenopausal status, hypertension, positive family history and time since last birth.

Although ovarian steroids are known to be key regulators of leiomyoma growth, altered expression of many protein-coding genes as well as genetic heterogeneity associated with chromosomal re-arrangements and mutation in a number of genes such as Mediator Complex Subunit 12 gene (MED12), fumarate hydratase (FH), High Mobility Group AT-Hook 2 (HMGA2) have also been associated with their development and growth progression. Recent studies have demonstrated that somatic MED12 mutations in exon 2 occurs at a frequency of up to 80% and have a functional role in leiomyoma pathogenesis potentially through activation of Wnt/β-catenin pathway MED12 is a component of Mediator complex which functions as a transcription coactivator by transmitting signals from transcription factors to RNA polymerase II.

Trp is an essential amino acid which is not only essential for protein synthesis and serotonin but also serves as a precursor of many important metabolites following its degradation which can occur through 4 pathways. Of these four pathways, the kynurenine degradation pathway which exists mainly in the liver holds the greatest importance accounting up to 95% of Trp degradation. The first step in the degradation of Trp is catalyzed by action of either TDO2 in the liver or IDO1 extra-hepatically to N-formylkynurenine which is then hydrolyzed to kynurenine by NFK formamidase. TDO2 is primarily localized in the liver although two variants have been identified in the mouse brain where it plays a role in development and in brain tumors.

IDO1 is ubiquitously distributed while a second isoform of IDO, IDO2 has lower catalytic activity, is expressed in kidney, liver, brain, and reproductive tract and has immunoregulatory function. An objective of this example was to characterize the expression and regulation of Trp catabolic enzymes in fibroids and their relevance to regulation of fibroid cell proliferation and aberrantly expressed genes such as collagen type I (COL1A1) and type III (COL3A1). We hypothesized that Trp catabolic pathway plays a key role in the pathogenesis of fibroid tumors.

Material and Methods
Tissue Collection and Primary Cell Isolation

Portions of uterine leiomyomas and paired myometrium were obtained from patients (N=58) not on hormonal treatments for at least 3 months prior to surgery at Harbor-UCLA Medical Center with prior approval from the Institutional Review Board (#036247) at the Lundquist Institute at Harbor-UCLA Medical Center. Informed consent was obtained from all the patients participating in the study prior to surgery. The paired tissues were obtained from Caucasians (N=12 with 3 pairs kindly provided by Dr. Al Hendy at University of Chicago), African Americans (N=25) and Hispanics (N=21). Race/ethnicity data was obtained from the electronic medical records which are based on self-report. The Hispanic group was entirely composed of White Hispanics. The mean age of patients was 45±4.8 years with a range of 35-54 years. The menstrual cycle phase was determined by histologic analysis of hematoxylin and eosin stained endometrial sections with 27 specimens being identified as in the proliferative phase and 14 specimens in the secretory phase.

The MED12 mutation status was determined by PCR amplification and Sanger sequencing. Of the specimens sequenced, 40 fibroids had the MED12 mutations (68.9%) with no mutations in the myometrium. Missense mutations in MED12 exon 2 were the most frequent alteration (85%), followed by in-frame insertion-deletion type mutations (15%). The missense mutations in exon 2 included c.130G>C (p.Gly44Arg) (11.8%), c.130G>A (p.Gly44Ser) (23.5%), c.130G>T (p.Gly44Cys) (8.8%), c.131G>C (p.Gly44Ala) (2.9%), c.131G>A (p.Gly44Asp) (35.3%), and c.131G>T (p.Gly44Val) (17.6%). The leiomyomas used in this study ranged in size from 2 to 5 cm in diameter and were intramural. The tissues were either snap frozen and stored in liquid nitrogen for further analysis or used for isolation of MSMC and LSMC. Briefly, LSMC were cultured in DMEM supplemented with 10% fetal bovine serum until reaching confluence with a change of media every 2-3 days. Cells at passages p1 to p3 were used for all experiments. Cell culture experiments were performed at least three times using MSMC and LSMC obtained from different patients. Overall, 8 LSMC and 10 MSMC were used for the in vitro experiments. All supplies for the isolation and cell culture were purchased from Sigma-Aldrich (St. Louis, MO), Invitrogen (Carlsbad, CA) and Fisher Scientific (Atlanta, GA).

RNA Isolation and qPCR Analysis

Total RNA was isolated from leiomyoma and matched myometrium using Trizol (Thermo Scientific, Waltham, MA) and RNA concentration and integrity was determined using a Nanodrop 2000c spectrophotometer (Thermo Scientific) and Agilent 2100 Bioanalyzer (Agilent Technologies, Santa Clara, CA) according to manufacturer's protocols. Subsequently, RNA sample of 1 µg each was reverse transcribed using random primers for IDO1 and TDO2. Quantitative PCR was carried out using SYBR gene expression master mixes (Applied Biosystems, Carlsbad, CA). Reactions were incubated for 10 min at 95° C. followed by 40 cycles for 15 seconds at 95° C. and 1 min at 60° C. mRNA levels were quantified using the Invitrogen StepOne System and normalized to FBXW2. All reactions were run in triplicate and relative expression was determined using the comparative cycle threshold method ($2^{-\Delta\Delta Cq}$), as recommended by the supplier (Applied Biosystems). Abundance values was expressed as fold change compared to the corresponding control group.

MED12 Mutation Analysis

Genomic DNA from leiomyomas and paired myometrial specimens was extracted from 100 mg of freshly frozen tissue using Tissue Genomic DNA Miniprep Kit (Bioland Scientific LLC, Paramount, CA), according to the manufacturer's protocol. PCR amplification and Sanger sequencing (Laragen Inc. Culver City, CA) was performed to investigate the MED12 exon 2 mutations. PCR products were sequenced using Big Dye Terminator v.3.1 sequencing chemistry and the sequences were analyzed with the Software ChromasPro 2.1.8 and compared with the MED12 reference sequence (NG 012808 and NM_005120).

Measurement of Kynurenine

Kynurenine concentration in paired leiomyoma and myometrium homogenates (N=46) was measured in duplicate using the Human Kynurenine ELISA kit (MB S766153; MyBioSource, San Diego, CA) according to the manufacturer's instructions. Absorbance of each plate was measured spectrophotometrically at a wavelength of 450 nm and the concentration was determined by comparing the optical density value of samples to the standard curve.

Immunoblotting

Total protein isolated from paired tissue samples and MSMC and LSMC spheroids following treatment conditions was subjected to immunoblotting. Briefly, samples were suspended in RIPA buffer containing 1 mM EDTA and EGTA (Boston BioProducts, Ashland, MA) supplemented with 1 mM PMSF and a complete protease inhibitor mixture (Roche Diagnostics, Indianapolis, IN), sonicated, and centrifuged at 4° C. for 10 min at 14,000 rpm. The concentration of protein was determined using the BCA™ Protein Assay Kit (Thermo Scientific Pierce, Rockford, IL). Equal aliquots (thirty micrograms) of total protein for each sample was denatured with SDS-PAGE sample buffer and separated by electrophoresis on a SDS polyacrylamide gel. After transferring the samples to a nitrocellulose membrane, the membrane was blocked with TBS-Tween+5% milk and probed with the following primary antibodies: IDO1 (Cell Signaling Technology, Danvers, MA), TDO2, COL3A1 (Proteintech Group, Inc, Chicago, Illinois) and COL1A1 (Fitzgerald Industries Intl, Acton, MA). The membranes were washed with TBS containing 0.1% Tween-20 wash buffer after each antibody incubation cycle. SuperSignal West Pico Chemiluminescent Substrate™ (Thermo Scientific Pierce) was used for detection, and photographic emulsion was used to identify the protein bands, which were subsequently quantified by densitometry. The membranes were also stripped and probed with glyceraldehyde 3-phosphate dehydrogenase (GAPDH) antibody (Santa Cruz Biotechnology, Santa Cruz, CA) serving as the loading control. The densities of the specific protein bands were determined using image J program (imagej.nih.gov/ij/), normalized to GAPDH or a band obtained from staining the membrane with Ponceau S. Results were expressed as means±SEM as a ratio relative to the control group designated as 1.

Immunohistochemistry

Paired myometrium and leiomyoma were fixed with 4% paraformaldehyde in PBS, and subsequently transferred to PBS containing 30% sucrose (wt/vol) until equilibrated in cold (4° C.). After fixation, 5-µm-thick paraffin sections were treated three times with Histo-Clear™ (National Diagnostics, Atlanta, GA) for 5 min, and rehydrated by a sequential ethanol wash, and then incubated in target retrieval solution (Dako, Carpinteria, CA) in a microwave for 8 min in order to retrieve the antigens. For blocking, tissues were incubated for 10 minutes with 3% solution of $H_2O_2$ followed by incubation with PBS-5% normal goat serum-0.2% Triton X-100. Tissue sections were incubated with primary antibody rabbit anti-IDO1 (dilution 1:200, Cell Signaling Technology) and anti-TDO2 (dilution 1:200, Proteintech Group, Inc) overnight at 4° C. in a humidified chamber. The antigens were then visualized using biotinylated antibodies and streptavidin, conjugated with horseradish peroxidase. Control sections were incubated with the secondary antibody, with replacement of primary antibody with the dilution reagent (Dako). Diaminobenzidine (Dako) served as the substrate, and all sections were counterstained with hematoxylin and eosin. Immunostained sections were examined under a microscope (Axioskop 40; Carl Zeiss Microimaging LLC, Thornwood, NY) at 40× magnification.

Spheroid Cell Culture

Isolated MSMC and LSMC were plated in 6-well (1×10$^5$ cells/well) or 96-well (5×10$^3$ cells/well) plates which were coated with 0.5% agarose gel and incubated 48 hours for spheroids formation.

Cell Proliferation Assay

The MSMC and LSMC spheroids were treated with different doses of IDO1 inhibitor (Epacadostat; Cayman Chemical, Ann Arbor, MI) and TDO2 inhibitor (680C91; Sigma-Aldrich) for 48 hours. The concentrations of inhibitors used was based on earlier studies and the cell proliferation was determined using the CellTiter-Glo 3D Cell Viability Assay (Promega, Madison, WI) according to the manufacturer's protocol. The assay was performed in six replicates per condition and repeated four times using cells isolated from four different patients.

Statistical Analysis

Throughout the text, all data are presented as mean±SEM and analyzed by PRISM software (Graph-Pad, San Diego, CA). Dataset normality was determined by the Kolmogorov-Smirnoff test, Shapiro-Wilk test, D'Agostino & Pearson test and Anderson-Darling test. Data presented in FIGS. 1-3 were not normally distributed and therefore non-parametric tests were used for data analysis. Comparisons involving two groups were analyzed using Wilcoxon matched-pairs signed rank test (FIG. 1) or Mann Whitney test (FIG. 2 and FIG. 3) as appropriate. Data presented in FIG. 4 were normally distributed and analyzed by one-way ANOVA. Statistical significance was established at $P<0.05$.

Results

Using paired leiomyoma and matched myometrium (N=58) the mRNA expression of IDO1, IDO2 and TDO2 in the same specimens was determined. Because of low to undetectable levels of IDO2 expression in these tissues we focused on determination of IDO1 and TDO2 expression in this study. The expression of IDO1 (60.3%, 35/58 pairs) and TDO2 (98.3%, 57/58 pairs) mRNA in fibroids as compared with myometrium was significantly higher (FIG. 1A). The degree of mRNA upregulation and the number of specimens exhibiting increased expression was significantly greater for TDO2 as compared to IDO1 (FIG. 1A). The levels of kynurenine, a marker of enzyme activity for IDO1/TDO2 was significantly higher in extracts of leiomyoma as compared with matched myometrium (FIG. 1B; 78.3%, 36/46 pairs). The IDO1 and TDO2 protein levels are shown in FIG. 1C-E. As demonstrated in this figure the IDO1 (FIG. 1C-D; 54%, 27/50 pairs) and TDO2 (FIGS. 1C and 1E; 92%, 46/50 pairs) protein abundance was significantly greater in leiomyoma as compared to matched myometrium. Immunohistochemical analysis confirmed the Western blots analysis and demonstrated both IDO1 and TDO2 were localized predominantly in the smooth muscle cells with greater expression in fibroid as compared with myometrium. Both enzymes were also localized with less staining intensity in fibroblasts, lymphocytes, and vascular endothelial cells (FIG. 1F).

The expression analysis of IDO1 and TDO2 mRNA based on race/ethnicity, cycle phase and MED12 mutation status are shown in FIG. 2. The expression of TDO2 in terms of fold change (leiomyoma vs. matched myometrium) indicated significantly greater expression of TDO2 mRNA in AA (N=25) as compared with Caucasian (N=12) and Hispanic groups (N=21), with no significant race-dependent differences in IDO1 mRNA expression (FIG. 2A-B). There were no menstrual cycle phase dependent differences in the expression of IDO1 and TDO2 mRNA (FIG. 2C-D). Because somatic MED12 mutations in exon 2 occur at high frequency in leiomyomas, we analyzed our data based on the MED12 mutation status. This analysis indicated that TDO2 mRNA but not IDO1 mRNA was expressed in greater abundance in tumors bearing the MED12 mutation (N=39) as compared with wild type tumors (N=19) (FIG. 2E-F). There were no correlations between the expression of TDO2 mRNA and different types of MED12 missense mutations in the specimens analyzed.

The protein expression of IDO1 and TDO2 was also analyzed based on race/ethnicity, menstrual cycle phase and MED12 mutation status. As shown in FIG. 3, race/ethnicity (FIG. 3A), menstrual cycle phase (FIG. 3C) and MED12 mutation status (FIG. 3E) did not influence IDO1 protein expression. There were no significant effects of race/ethnicity (FIG. 3B) or menstrual cycle phase (FIG. 3D) on TDO2 protein levels. However, in agreement with the mRNA analysis, TDO2 protein levels were significantly higher in fibroid tumors bearing the MED12 mutation as compared with wild type tumors (FIG. 3F).

Figure 4E:
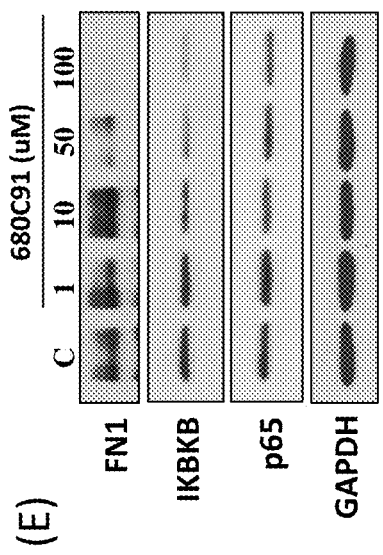

The functional relevance of IDO1 and TDO2 in fibroid pathogenesis was determined by the influence of these enzymes on MSMC/LSMC spheroids cell proliferation and expression of extracellular matrix (ECM) proteins. The effects of inhibitors of IDO1 and TDO2 on MSMC and LSMC spheroids cell proliferation as determined by Cell-Titer-Glo 3D Cell Viability Assay are shown in FIG. 4A-B. The IDO1 inhibitor, Epacadostat in various concentrations had no effect on MSMC and LSMC spheroids cell proliferation (FIG. 4A). In contrast, the TDO2 inhibitor, 680C91 in various concentrations significantly inhibited LSMC but not MSMC spheroid cell proliferation (FIG. 4B). The IDO1 inhibitor Epacodostat did not have any effect on the expression of ECM proteins, COL1A1 and COL3A1 (FIG. 4C). However, inhibition of TDO2 by 680C91 significantly reduced the expression of COL1A1 and COL3A1 in LSMC spheroids with no significant effect on expression of these proteins in MSMC spheroids (FIG. 4D).

The results presented here demonstrate for the first time that the metabolism of Trp in fibroid tumors as characterized by the upregulation of the principal enzymes involved in its degradation is dysregulated. The levels of kyneurenine, a marker of IDO1/TDO2 enzyme activity as expected was higher in fibroids as compared to myometrium. The upregulation of TDO2 protein and mRNA in most specimens analyzed, the degree of its upregulation and the response to its inhibition on cell proliferation and ECM proteins as compared to IDO1 suggest a greater significance of TDO2 dysregulation relative to IDO1 in fibroid pathogenesis. The upregulation of TDO2 but not IDO1 mRNA in fibroids was dependent on race. Furthermore, TDO2 but not IDO1 mRNA and protein levels were more abundant in tumors bearing the MED12 mutation. The race and MED 12 dependent expression of TDO2 further point to the physiological relevance of TDO2 dysregulation to fibroid pathology. The pharmacologic inhibition of TDO2 but not IDO1 in MSMC and LSMC spheroids led to selective inhibition of cell proliferation and expression of COL1A1 and COL3A1 in LSMC spheroids but not MSMC spheroids cultures.

A number of findings here point to a greater relevance of TDO2 overexpression relative to IDO1 in fibroid pathogenesis. These factors include 1). Universal overexpression of TDO2 mRNA/protein in the specimens analyzed, 2). A far greater fold increase in TDO2 relative to IDO1 in fibroids, 3). Race and MED12 dependence of TDO2 but not IDO1 expression in fibroids and 4). Responsiveness to the TDO2 but not IDO1 inhibitor in terms of inhibition of LSMC cell proliferation and expression of COL1A1 and COL3A1. The lack of response to IDO1 inhibitor may be because the upregulation of the enzyme occurred only in a limited number of specimens, or the degree of upregulation was not as pronounced as for TDO2, and or the possibility that the inhibitor used lacked the necessary potency. Based on our current findings targeting TDO2 inhibition rather than IDO1 holds a greater promise for therapeutic purposes.

In summary, this example provides evidence for a marked dysregulation of Trp catabolism in fibroid tumors. The data indicates a marked upregulation of TDO2 protein and mRNA and to a lesser degree and in a more limited number of specimens, IDO1 mRNA and protein. The expression of TDO2 but not IDO1 was race and MED12 dependent. Pharmacologic inhibition of TDO2 but not IDO1 inhibited LSMC but not MSMC spheroids cell proliferation and expression of COL1A1 and COL3A1. These results suggest that targeted inhibition of TDO2 can have therapeutic benefit for treatment of fibroids.

Example 4: Additional Mechanistic Studies

This example adds additional mechanistic studies relating to dysregulated tryptophan catabolism in leiomyomas.

Using fresh leiomyoma explants, we confirmed that the expression of COL1A1 and COL3A1 was decreased in culture-conditioned media following treatment with different doses of TDO2 inhibitor, 680C91 (FIG. 5A). Additionally, treatment of primary leiomyoma spheroid cells with 17β-Estradiol (E2) and progesterone (P4) up-regulated IDO1 and TDO2 expression (FIG. 5B), indicating they are under ovarian steroids regulation. Knockdown of endogenous miR-200c by transfection with anti-miR-200c oligonucleotides in LSMC spheroids cells resulted in upregulation of TDO2 expression (FIG. 5C-D), suggesting TDO2 is a target of miR-200c in leiomyoma. Knockdown of TDO2 by its specific siRNAs in primary LSMC spheroid cells led to elevated expression of miR-29c and miR-200c (FIG. 5E-F), indicating a potential mechanism linking these miRNAs with TDO2 dysregulation in leiomyomas.

In addition, the expression of CYP1B1, a downstream marker of AhR signaling pathway activation was significantly increased in leiomyoma (FIG. 6A, N=43). We also demonstrated the increased nuclear levels of AhR and ARNT in leiomyoma as compared to matched myometrium indicative of nuclear translocation of AhR in fibroids (FIG. 6B). Using fresh leiomyoma explants we confirmed that the expression of CYP1B1 was increased by the treatment of kynurenine (Kyn) and tryptophan, while decreased following TDO2 inhibitor treatment (FIG. 6C). Treatment of LSMC spheroids cells with Kyn to mimic what might be occurring in vivo, demonstrated an increase in the expression of AhR, IDO1, TDO2 and COL1A1 (FIG. 6D). This data suggests the intriguing possibility for the presence of a positive feedback loop in fibroids, wherein activation of the AhR signaling pathway results in increased expression of TDO2/IDO1 thus setting up a vicious cycle for constant activation of this signaling pathway and progression of ECM accumulation.

Figure 7E:
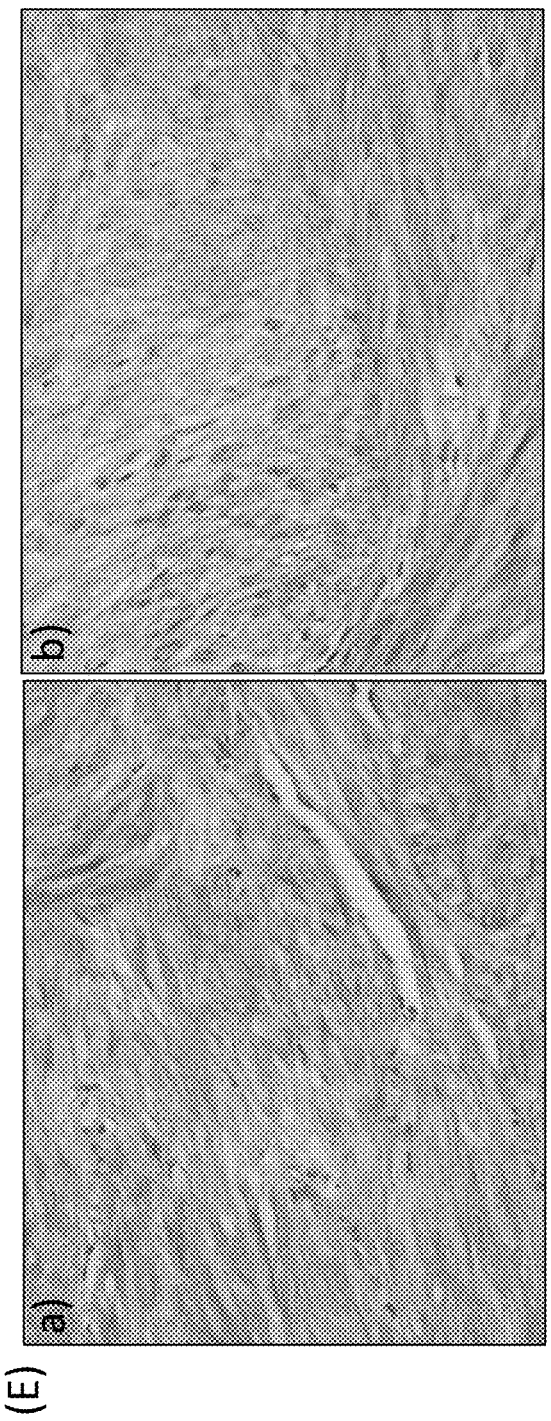

We also performed the in vivo experiment using freshly collected leiomyoma explants implanted subcutaneously in the flank of ovariectomized CB-17 scid/beige female mice (N=6), and treated with vehicle or TDO2 inhibitor (680C91; 10 mg/Kg daily, i.p.) for 8 weeks (FIG. 7A). After sacrifice, the explants weight was determined and the collected plasma was analyzed for levels of tryptophan, kynurenine and blood chemistry panel (Abaxis). The results showed the TDO2 inhibitor treated explants had lower weight (FIG. 7B) and decreased the ratio of kynurenine/tryptophan (FIG. 7C). There were no adverse effects on blood chemistry including liver and renal panels. Furthermore, there were no effects on body weight or food consumption in animals treated with the inhibitor indicating drug safety albeit based on a limited number of mice. Following treatment with the TDO2 inhibitor, the expression of genes related to extracellular matrix (COL1A1 and FN1), epigenetic regulation (DNMT1) and cell growth (CCND1) were down-regulated (FIG. 7D). In addition, Masson's Trichrome staining showed less deposition of collagens (blue), keratin (red) and cytoplasm (red) in TDO2 inhibitor treated explants (FIG. 7E), thus further supporting its usefulness for fibroid therapy.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A method of treating fibroid in a patient in need thereof, comprising administering to the patient a therapeutically effective amount of 680C91.

2. The method of claim 1, wherein the 680C91 does not reduce estrogen or progesterone in the patient.

3. The method of claim 1, wherein the fibroid is a uterine fibroid.

4. The method of claim 3, wherein the uterine fibroid is selected from the group consisting of intramural fibroid, subserosal fibroid, subserosal tumor, or submucosal fibroid.

5. The method of claim 3, which ameliorates at least a symptom selected from the group consisting of heavy bleeding between or during periods that includes blood clots, pain in the pelvis or lower back, increased menstrual cramping, increased urination, pain during intercourse, menstruation that lasts longer than usual, pressure or fullness in your lower abdomen, and swelling or enlargement of the abdomen.

6. The method of claim 3, wherein the patient is African American or Hispanic.

7. The method of claim 1, wherein the administration is oral, intravenous, intramuscular, subcutaneous, or local injection to the fibroid.

* * * * *